(12) United States Patent
Freeman

(10) Patent No.: US 10,350,251 B2
(45) Date of Patent: Jul. 16, 2019

(54) MEDICAL COMPOSITIONS, METHODS OF MAKING AND USING THOSE COMPOSITIONS, AND KITS INCLUDING THOSE COMPOSITIONS

(71) Applicant: Keith Gerald Freeman, Los Gatos, CA (US)

(72) Inventor: Keith Gerald Freeman, Los Gatos, CA (US)

( * ) Notice: Subject to any disclaimer, the term of this patent is extended or adjusted under 35 U.S.C. 154(b) by 0 days.

(21) Appl. No.: 13/986,100

(22) Filed: Mar. 28, 2013

(65) Prior Publication Data
US 2013/0295172 A1 Nov. 7, 2013

Related U.S. Application Data

(60) Provisional application No. 61/685,956, filed on Mar. 28, 2012.

(51) Int. Cl.
| | |
|---|---|
| *A61K 36/185* | (2006.01) |
| *A61K 31/352* | (2006.01) |
| *A61J 3/00* | (2006.01) |
| *A61J 3/10* | (2006.01) |
| *A61K 9/48* | (2006.01) |

(52) U.S. Cl.
CPC ............... *A61K 36/185* (2013.01); *A61J 3/00* (2013.01); *A61J 3/10* (2013.01); *A61K 9/4875* (2013.01); *A61K 31/352* (2013.01)

(58) Field of Classification Search
CPC .................................................. A61K 31/352
See application file for complete search history.

(56) References Cited

U.S. PATENT DOCUMENTS

2007/0072939 A1* 3/2007 Kupper ............... A61K 31/353
514/454
2011/0097283 A1* 4/2011 Van Damme ........ A61K 9/0058
424/48

OTHER PUBLICATIONS

Cannaleve Flickr, http://www.flickr.com/photos/66746928@N06/6561484135/in/photostream/, published Dec. 23, 2011, 1 page.*
Cannabis capules, http://boards.cannabis.com/concentrates/140616-cannabis-capsules-step-step-guide.html, Nov. 12, 2007, 18 pages.*
Stickyguide, Cannaleve Indica 30mg 10pk, https://www.stickyguide.com/dispensaries/berkeley-patients-group/products/cannaleve-indica-30mg-10pk--2, 2014, 1 page.*
Grasscity, 3 pages, 2010.*
Rollitup, 3 pages, 2009.*
420 magazine, https://www.420magazine.com/community/threads/how-do-i-make-medical-marijuana-capsules.72228/, 2007, 5 pages.*

* cited by examiner

*Primary Examiner* — Kyle A Purdy
(74) *Attorney, Agent, or Firm* — E. Thomas Wheelock; Marie E. Sobieski

(57) ABSTRACT

Disclosed here are compositions comprising powdered hemp seed, an emulsifier/dispersant such as lecithin (particularly soya lecithin), *cannabis*, and optionally other additives and excipients. Also described are methods of making the compositions. The compositions may be used, for instance, in the treatment of pain and for their anti-emetic (anti-nausea and anti-vomiting) properties, as well as for the treatment of anorexia and appetite enhancement. Kits containing the compositions, arranged for proper sequential dosing, and optionally including instructions for use are also disclosed.

27 Claims, No Drawings

MEDICAL COMPOSITIONS, METHODS OF MAKING AND USING THOSE COMPOSITIONS, AND KITS INCLUDING THOSE COMPOSITIONS

RELATED APPLICATIONS

This patent application claims priority to U.S. Provisional Patent Application Ser. No. 61/685,956, entitled "Medical Compositions, Methods of Making and Using Those Compositions, And Kits Including Those Compositions" filed on Mar. 28, 2012, which application is hereby incorporated by reference in its entirety for all purposes.

FIELD

Disclosed here are compositions comprising powdered hemp seed, an emulsifier/dispersant such as lecithin (particularly soy lecithin), cannabis, and optionally other additives and excipients. Also described are methods of making the compositions. The compositions may be used, for instance, in the treatment of pain and for their anti-emetic (anti-nausea and anti-vomiting) properties, as well as for the treatment of anorexia and appetite enhancement. Kits containing the compositions, arranged for proper sequential dosing, and optionally including instructions for use are also disclosed.

BACKGROUND

Cannabinoids of natural origin are compounds derived from plants commonly known as marijuana. Among the several dozen cannabinoid compounds characterizing marijuana, tetrahydrocannabinols (THC), and $\Delta^9$-tetrahydrocannabinol ($\Delta^9$-THC) in particular, are considered to be those most active. These compounds possess several properties, e.g., an analgesic effect, an anti-inflammatory activity, the reduction of the blood and intraocular pressure, and an antiemetic activity, that may be therapeutic both in mammals and in human beings.

Additionally, such preparations derived from natural origin have been effectively used as anti-emetics for treatment of nausea and vomiting and for enhancement of appetite, mainly in AIDS patients. (Mechoulam, R., "Cannabinoids as Therapeutic Agents" CRC Press, Boca Raton, Fla. 1-19, 1986).

The pharmacological action of cannabinoids appears directly correlated to their affinity towards two different classes of specific receptors belonging to the family of the "G protein-coupled" receptors: the CB1 receptors, located in the central nervous system besides that in peripheral tissues, and the CB2 receptors, found in the cerebellum (Q. J. Lu et al.; *Visual Neurosci.;* 2000, 17, 91-95) but which are mostly found in peripheral tissues (M. Glass; *Progr. Neuro-Psychopharmacol. &Biol. Psychiat.;* 2001, 25, 743-765). In the brain, the CB1 receptors are found in the hippocampus, in the cortical regions, in the cerebellum, and inside the basal ganglia. Among the peripheral tissues wherein the CB1 receptors have been found, the testicles, the small intestine, the vesica, the deferent duct can be mentioned. CB1 receptors have also been identified in the human eye, variously in the retina, in the iris, and in the ciliary body (A. Porcella et al.; *Molecular Brain Research;* 1998, 58, 240-245; A. Porcella et al.; *European Journal of Neuroscience;* 2000, 12, 1123-1127).

The CB2 receptors are largely located in the marginal zones of the spleen, in tonsils, in several cells of the immune system, as macrophages, monocytes, the cells of the bone marrow, of thymus, and of pancreas. Other cells of the immune system having CB2 receptors are T4 and T8 cells, the polymorphonucleated leucocytes, in particular the cells called "natural killers" and lymphocytes B.

The native active constituent, delta 9-tetrahydrocannabinol ($\Delta^9$-THC), is synthetically produced, prescribed, and sold today. In the U.S. and Canada, ($\Delta^9$-THC) is nominated as "dronabinol" under the mark "MARINOL®" by Solvay Pharmaceuticals and, under license, by PAR Pharmaceuticals. The U.S. Food and Drug Administration has approved MARINOL® for the treatment of anorexia and wasting in AIDS patients, as well as for refractory nausea and vomiting by patients undergoing chemotherapy.

DESCRIPTION

Disclosed here are compositions comprising *cannabis*, an emulsifier/dispersant such as lecithin (particularly soya lecithin), natural marijuana components, and optionally other additives and excipients. Methods of making the compositions are also described. The compositions may be used, for instance, in the treatment of pain and for their anti-emetic (anti-nausea and anti-vomiting) properties, as well as for the treatment of anorexia and appetite enhancement. Kits containing the compositions, arranged for proper sequential dosing, and optionally including instructions for use are also disclosed.

COMPOSITIONS

My compositions comprise hemp seed powder, one or more emulsifiers/dispersants such as lecithin (particularly soya lecithin), *cannabis*, and (optionally) other additives and excipients.

Hemp Seed Powder

Hemp seed powder is added to my compositions to provide a measure of dispersion and dilution to the natural *cannabis* component. Because hemp seed powder is derived from a plant related to cousins—*cannabis sativa* and *cannabis indica*—the hemp seed powder and *cannabis* components blend together well. In addition to acting as a dispersal medium for the *cannabis* concentrate, the hemp seed powder contains beneficial protein, fats, fiber, and omega-3 and -6 fatty acids.

The powder may be formed by communition, e.g., by grinding or milling or other suitable procedure, of the seed to a fine powder having a particle size between that of powdered sugar to granulated sugar. The particle size is not particularly important and is selected to provide adequate dispersal of the other components in my composition.

Although a variety of hemp seed powders may be utilized in my compositions, I prefer to use powders often sold as hemp seed protein or hemp seed flour and is formed by cold-processing raw, live hemp seeds. Those cold processing steps include a mechanical step of removing the hard shells from the hemp seed's ("dehulling") and mechanically pressing the dehulled hemp seeds, e.g., by expeller expressing the seed cores without hexane or other solvents, to remove hemp oil from the seeds and to form a seed cake. Dehulling the seeds reduces the crude fiber content of the seed cake while increasing the protein concentration of the remaining seed meats. The seed cake is then milled or otherwise reduced to particulate form to produce my preferred hemp seed powder.

I prefer to utilize hemp seed powder that is also certified organic and is otherwise free of pesticides and the like.

Although my preferred hemp seed powder is that described just above, hemp seed powder produced by other procedures may also be utilized with lesser effect. For instance, the following steps may be used to process hemp seed to separate the included hemp oil from the seed cake used to prepare hemp seed powder: preparation, cracking and dehulling, conditioning, milling, flaking or pressing, and extracting. Each of these steps will be discussed in more detail herein below. These steps are currently used in the commercial separation of seed oils. A person of ordinary skill would know that the steps may be combined, used in a different order, or otherwise modified.

Generally, the preparation step includes an initial cleaning process, which removes stones, dirt, foreign bodies, and other debris collected during the harvest and storage of the seeds. Removal of such extraneous matter may positively affect the quality of the final hemp seed powder by removing compounds that negatively impact its chemical stability. Preferably, ripe, unbroken seeds are used. These seeds have reduced levels of chlorophyll and reduced levels of free fatty acids.

After the preparation step, the seeds may then be cracked and dehulled. Cracking and dehulling may be accomplished in a variety of ways. For example, the seeds may be cracked and dehulled using a seed cracker, which mechanically breaks the hemp seeds, releases the hulls, and directly exposes the inner seed meat to air. After cracking, the hulls may be separated from the seed meats by a dehuller. The dehuller typically separates the hulls from the seed meats using the density difference between the hulls and the seeds. The hulls are not as dense as the seed meats. For example, a dehuller using aspiration or air flotation will separate the hulls from the cracked seed meats. Optionally, after dehulling, the hulls may be sieved to recover small seed meat particulates, or fines, generated during cracking of the seeds. After recovery, the fines may be added to the seed meats prior to the conditioning step.

Once the seeds are cracked, it is desirable to minimize the exposure of the seed meats to oxygen to reduce oil oxidation and improve the quality of the seed cake. It is desirable to minimize oxygen exposure independently in each of the described processing steps.

Once the seeds are cracked and dehulled, they may be subjected to a conditioning step to make the seed meats pliable prior to further processing. Conditioning also ruptures oil bodies in the seed meats. Further processing, e.g., by flaking, grinding or other milling technology, is made easier by having pliable seed meats at this stage. If necessary, moisture typically is removed from or added to the seed meats to achieve a 6-10 wt. % moisture level. If moisture is removed, this process step is called toasting and if moisture is added, the process step is called cooking. Typically, the seed meats are heated to 40-90° C. with steam which is dry or wet depending on the direction of adjustment of the moisture content of the seed meats. As noted above, the conditioning step should take place under conditions minimizing oxygen exposure.

Once the seed meats are conditioned, they may be milled to a desired particle size or flaked to a desired surface area. Again, the flaking or milling steps may be carried out under conditions minimizing oxygen exposure. Flaking or milling is done to increase the surface area of the seed meats and also to further rupture the oil bodies in the seed body thereby facilitating a more efficient extraction.

Any of a variety of milling technologies is appropriate and is well known. The considerations when choosing a method of milling and a resulting particle size include the oil content in the seed and the desired efficiency of the extraction of the seed meats or the seed. When flaking the seed meats, the flakes may typically be from about 0.1 to about 0.5 mm thick.

Optionally, after the seed meats are milled, they may be pressed to lower their oil content. Seed meats are often pressed when the oil content of the seed meats is greater than about 30%, by weight. However, seed with higher or lower oil contents may be pressed as well. The seed meats may be pressed, for example, in a hydraulic press or mechanical screw. The seed meats may be heated to a temperature, e.g., of less than about 55° C., during pressing.

After pressing, the resulting hemp oil may be passed through a screen, collected, and filtered. The oil collected in this step is called "first press oil." The so-pressed seed meats are called "seed cake." The seed cake may contain residual oil. The seed cake may optionally be subjected to a solvent extraction step or steps. Compositions that include seed cakes that have been subjected to solvent extraction are within the scope of my invention.

That residual hemp oil may be extracted from the seed meats or seed cake by contact with an effective solvent. Aliphatic solvents, such as n-hexane and iso-hexane are effective solvents for extracting the remaining oil. Such aliphatic solvents are desirably degassed prior to contact with the seed cake. Such an extraction may be carried out in a variety of ways; e.g., the extraction may be a batch or continuous, co-current or counter-current in nature. After extraction, the solvent may separated from the hemp oil by, e.g., distillation, evaporation, stripping, etc. The solvent may be removed from the seed cake by heating or vacuum stripping. Great care should be taken to remove all vestiges of the solvent should these procedures be selected.

If necessary, the seed cake may finally be comminuted, e.g., by grinding or milling or other suitable procedure, to a fine powder as discussed above.

Lecithin

The second component of my composition comprises lecithin, typically or desirably soy lecithin. The soy lecithin powder acts as an emulsifier, dispersant, and stabilizer that evenly disperses the hemp seed powder and the *cannabis* concentrate and gives my formulation a consistent texture. The lecithin further acts as a carrier for the *cannabis* cannabinoids present in my composition to pass through the intestinal mucosa into the bloodstream.

Preferably, my composition contains a soy-derived lecithin in powder form that has been de-oiled and, for the purposes of mixing the composition, of size 35-40 mesh. Preferably, the lecithin is certified organic and completely pesticide-free.

Although soy lecithin as described just above is preferred, other lecithins may be included with or in lieu of soy lecithin. For instance, sunflower-based and egg-based lecithins are also acceptable.

Generally, lecithin refers to a group of yellow-brownish fatty substances occurring in animal and plant tissues made up of phosphoric acid, choline, fatty acids, glycerol, glycolipids, triglycerides, and phospholipids (e.g., phosphatidylcholine, phosphatidylethanolamine, and phosphatidylinositol). The principal phospholipids in soy and sunflower lecithin are phosphatidylcholine, phosphatidylinositol, phosphatidylethanolamine, and phosphatidic acid.

Cannabis

My composition comprises a third component denoted "*cannabis*," which refers to natural compositions, typically resinous in nature, containing active cannabinoids, particularly THC (or THCA), separated from marijuana plants. *Cannabis Indica* and *Cannabis Sativa* are two strains of the marijuana plant. In addition to the medical benefits detailed elsewhere herein, each strain has its own individual psychoactive properties. The Indica strain is typically used for relaxation, stress and pain relief, and to provide a sense of calm and serenity. The Sativa typically produce a more energetic cerebral effect, often characterized as uplifting and stimulating, as well as providing pain relief.

The *cannabis* component includes hair-like, translucent resin glands known as trichomes that naturally protrude from the buds, leaves, and other sites on the plant. The *cannabis* component may include other portions of the *cannabis* or marijuana plant in addition to the resin.

The concentrate or *cannabis* component may be made using a process designed to extract and preserve the psychoactive resins from the *cannabis* plant. The process includes steps of immersing, chilling, and agitating in ice water. The *cannabis* leaf, flowers, buds, etc. are first chopped and then mixed into an ice and water bath; the mixture is agitated in a manner similar to a washing machine. The cold water and ice harden the resins and cause them to break off from the plant leaves and buds.

The hardened particulates containing the resins are separated from the water bath and are used as the *cannabis* concentrate or composition. The leaves, buds, etc. are also separated from the water. Extraneous leaves may be separated from the hardened resins. Some variations of this procedure produce a mixture known as "cold water hash."

The resulting *cannabis* component is measured for: 1.) potency (e.g., weight percentage of ($\Delta^9$-THC)), 2.) pesticide residues, and 3.) colony-forming unit (CFU) counts. *Cannabis* concentrates having any pesticide residues or that exhibit CFU counts above 200,000 are rejected.

Determination of the potency of the *cannabis* component allows production of doses having specific, predetermined amounts of THC, as discussed below.

Excipients

My compositions or formulations may optionally contain one or more excipients. Examples of such excipients include, for instance:
1.) diluents (or vehicles or disintegrating agents) such as starches; agar; microcrystalline cellulose; sugars such as lactose, dextrose, glucose, mannitol, sucrose, sorbitol; gelatin, gums such as acacia and tragacanth gums, dicalcium phosphate, tricalcium phosphate, monocalcium phosphate, sodium phosphate, sodium carbonate, calcium citrate, calcium carbonate, sodium bicarbonate, carboxymethyl cellulose, pregelatinized corn starch, pregelatinized starch, celluloses, cross-linked carboxymethylcellulose, cross-linked polyvinylpyrrolidone, calcium-sodium alginate complexes, clays, alginates, sodium starch glycolate, and disintegration agents such as are used in tablet preparations;
2.) lubricants such as talc, stearic acid, zinc stearate, calcium stearate, magnesium stearate, polyethylene glycols, silica, and hydrogenated vegetable oils and similar materials;
3.) binders such as acacia, alginic acid and salts thereof; sucrose, glucose, various polyethylene glycols, polyvinylpyrrolidone, cellulose derivatives, ethyl cellulose, methyl cellulose, hydroxyethylcellulose, hydroxypropylcellulose, hydroxypropyl methylcellulose, magnesium aluminum silicate, tragacanth gums, corn or maize starch, shellac, gelatin, gum arabic, polyvinyl pyrrolidone, polyvinylpyrrolidone/vinyl acetate copolymers, polyvinyl alcohol, polyacrylic acid, polymethacrylates, polymethacrylic acid, polysaccharide acids, clays such as bentonites, sorbitol, pregelatinized starch and similar materials;
4.) colorants such as ferric oxides, FD&C dyes and similar materials;
5.) anti-oxidizing agents such as ascorbic acid, tocopherol, vitamin A, β-carotene, sodium hydrogen sulfite, sodium thiosulfate, sodium pyrosulfite, citric acid, and similar materials;
6.) flavoring agents;
7.) anti-aggregating agents such as stearic acid, talc, light anhydrous silicic acid, and hydrous silicon dioxide, and similar materials;
8.) absorption promoters, typically surfactants, such as higher alcohols, higher fatty acids, glycerin fatty acid esters, and similar materials;
9.) surfactants such as sodium lauryl sulfate, sorbitan monooleate, polyoxyethylene sorbitan monooleate, polysorbates, polaxomers, bile salts, glyceryl monostearate, and similar materials;
10.) solubilizing agents, often organic acids, such as fumaric acid, succinic acid, malic acid, and similar materials;
11.) stabilizers such as benzoic acid, sodium benzoate, ethyl parahydroxybenzoate, and similar materials;
12.) revitalizing ingredients such as creatine, taurine, vitamin $B_1$, vitamin B derivatives, amino acids and mixtures thereof, and similar materials;
13.) pH modifiers (or buffers) such as suitable organic acids or alkali metal salts of those organic acids. Suitable organic acids include benzoic acid, fumaric acid, malic acid, maleic acid, glutaric acid, citric acid, tartaric acid, succinic acid, adipic acid and the like. Examples of alkali metal salts of those organic acids include lithium, sodium, and potassium salts, in particular, the sodium salt of citric acid (i.e., sodium citrate).

Excipients may be included in the compositions in amounts between about 5% to 90% by weight, commonly less than about 15% by weight as appropriate or desired for the particular purpose.

Additionally, drug formulations are discussed in, for example, Remington's, The Science and Practice of Pharmacy (2000); Lieberman, H. A. and Lachman, L., Eds., Pharmaceutical Dosage Forms, Marcel Decker, New York, N.Y., 1980; and Liebeman et al., Pharmaceutical Dosage Forms (Volumes 1-3, 1990).

When the excipient serves as a diluent, it may be in the form of a solid, semi-solid or liquid material, which acts as a vehicle, carrier or medium for the active ingredient. Thus, the compositions may be in the form of a tablet, pill, powder, lozenge, sachet, cachet, troche, soft and hard gelatin capsule, sterile packaged powder, dispensable powder, or granule.

Method of forming the Composition

My compositions comprise or consist essentially of the 1.) *cannabis* component containing specific predetermined doses of THC, 2.) lecithin, and 3.) hemp seed.

Doses of my composition desirably are produced in the form of gel capsules or tablets containing a specific amount of THC. Therefore, it is necessary to first calculate and to provide a specific weight of the *cannabis* component (having a particular THC concentration), to provide a specific relative weight of the soy lecithin, and to provide the remainder of the composition in the form of the hemp seed powder.

These three components, optionally with any excipients, are then well-mixed desirably using a mechanical mixer.

The mixture is then finely ground and sifted. Any oversize particles are re-ground and recycled to the mixture. The mixture may be re-ground a sufficient number of times that a specific batch of the composition all passes through a small mesh screen.

The mixture is then heated to a temperature, e.g., between about 200° F. and about 250° F., for a short period of time, e.g., about 20-40 minutes, preferably about 30 minutes. The purpose of the heating step is to de-carboxylate the THC-carboxy molecule naturally occurring in the *cannabis* component and to convert it to the active THC form. The heating step additionally sterilizes the mixture.

After cooling, the mixture or composition may then be placed in the desired gel capsules or otherwise formed into suitably sized doses.

Forms

My compositions or formulations are typically provided in the form of a soft or hard-shelled gelatin or plant vegetarian gelatin capsule or an (optionally) coated tablet.

Soft and hard-shelled gelatin or plant vegetarian gelatin capsules are well known in the pharmaceutical art and need not be discussed additionally here. My compositions containing the components discussed above and made using the procedure also discussed above are simply introduced into the capsules for use.

Tablet forms of my composition or formulation may include, for example, one or more of lactose, mannitol, corn starch, potato starch, microcrystalline cellulose, acacia, gelatin, colloidal silicon dioxide, talc, magnesium stearate, stearic acid, and other excipients, colorants, diluents, buffering agents, moistening agents, preservatives, flavoring agents and pharmaceutically compatible carriers.

One acceptable tablet manufacturing process may employ one or a combination of methods: (1) dry mixing, (2) direct compression, (3) milling, (4) dry or non-aqueous granulation, (5) melt granulation, or (6) fusion. See, Lachman et al., The Theory and Practice of Industrial Pharmacy (1986).

Such tablets may also comprise film coatings, which disintegrate upon oral ingestion or upon contact with diluent.

Compressed tablets are typically solid dosage forms prepared by compacting a formulation containing an acid-labile pharmaceutical agent and/or buffering agent and/or excipient selected to aid the processing and improve the properties of the product. The term "compressed tablet" generally refers to a plain, uncoated tablet for oral ingestion, prepared by a single compression or by pre-compaction tapping followed by a final compression.

The tablets or pills of the present invention may be coated or otherwise compounded to provide a dosage form affording the advantage of improved handling or storage characteristics. For example, the tablet or pill can comprise an inner dosage and an outer dosage component, the latter being in the form of an envelope over the former.

My compositions may be formed as rapidly disintegrating tablets or powders, chewable tablets, lozenges, troches, or swallowable tablets. Effervescent salts may be used to disperse medicines in water for oral administration. Effervescent salts are typically granules or coarse powders containing a medicinal agent in a dry mixture, usually composed of sodium bicarbonate, citric acid and tartaric acid. When the salts are added to water, the acids and the base react to liberate carbon dioxide gas, thereby causing "effervescence."

Many other types of release delivery systems are available and known to those of ordinary skill in the art. They include polymer-based systems, such as polylactic and polyglycolic acid, polyanhydrides and polycaprolactone; nonpolymer systems that are lipids, including sterols, such as cholesterol, cholesterol esters and fatty acids, or neutral fats, such as mono-, di- and triglycerides; hydrogel release systems; silastic systems; peptide-based systems; wax coatings; compressed tablets using conventional binders (See, for example, Lieberman et al., Pharmaceutical Dosage Forms, 2 Ed., Vol. 1, pp. 209-214 (1990)), and excipients; partially fused implants; and the like.

Administration

My compositions or formulations may be administered in a variety or ways depending in the main upon the selected physical form of the composition. The compositions may be administered, e.g., by oral administration, sublingual administration, transrectal administration, transvaginal administration, and transnasal administration. Among those methods, I have had good reception from patients taking hard-shelled gelatin or plant vegetarian gelatin capsules by oral administration.

Cannabinoid Acid Addition Salts

Certain natural cannabinoid compounds of the invention also form pharmaceutically acceptable salts, for example, acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic, and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. See, for example, S. M. Berge, et al., "Pharmaceutical Salts," J. Pharm. Sci., 66: 1-19 (1977).

Combination Therapy Compositions

My compositions may also be used in combination ("combination therapy") with another pharmaceutical agent or agents indicated for treating or preventing a selected disorder. Such added agents may include, for example, opioid or opiate analgesics, NSAIDs, COX-2 inhibitors, and anti-emetics (for example, ondansetron).

The phrase "combination therapy" is meant to include the administration of my composition in conjunction with another pharmaceutical agent that is indicated for treating or preventing a disorder in a subject, as part of a specific treatment regimen intended to provide a beneficial effect from the co-action of these therapeutic agents for the treatment of a disorder. The beneficial effect of the combination includes, but is not limited to, pharmacokinetic or pharmacodynamic co-action resulting from the combination of therapeutic agents. Administration of these therapeutic agents in combination may be carried out over a defined time period (usually substantially simultaneously, minutes, hours, days, weeks, months or years depending upon the combination selected). "Combination therapy" is not intended to encompass the administration of two or more of these therapeutic agents as part of separate monotherapy regimens that incidentally and arbitrarily result in the combinations claimed here. The term "Combination therapy" is intended to embrace administration of these therapeutic agents in a sequential manner, where each therapeutic agent is administered at a different time. The term is intended to include administration of these therapeutic agents, or at least two of the therapeutic agents, in a substantially simultaneous manner. Substantially simultaneous administration may be accomplished, for example, by administering to the subject a single tablet or capsule having a fixed ratio of each therapeutic agent or in multiple, single capsules, or tablets for each of the therapeutic agents. Sequential or substantially simultaneous administration of each therapeutic agent may be effected by any appropriate route.

For instance, my composition may be administered orally or via a suppository, while the other therapeutic agent of the combination is administered by any appropriate route for that particular agent, such as via an oral route, inhalation, a percutaneous route, an intravenous route, an intramuscular route, or by direct absorption through mucous membrane tissues.

The term "combination therapy" is also intended to include the administration of the therapeutic agents as described above in further combination with one or more other biologically active ingredients, such as pain relievers, such as steroidal or nonsteroidal anti-inflammatory drugs, or agents for improving stomach motility, for example, and with non-drug therapies such as surgery.

Kits

My compositions and formulations may be assembled in the form of a kit or package containing one or more of the compositions. My compositions and formulations may be packaged in the form of a kit or package in which hourly, daily, weekly, or monthly (or other periodic) dosages are arranged for proper sequential or simultaneous administration. This drug delivery system may be used to facilitate administration of any of the variations my compositions including, for instance, agents or compositions used in combination therapy to facilitate proper administration of the dosage forms. In one variation of my kit, the system contains a plurality of doses to be to be administered daily or as needed for symptomatic relief. The kit or package may also contain a set of instructions for the subject.

Definitions

The use of the term "about" in the present disclosure means "approximately," e.g., +/−5% of the component referred to, and use of the term "about" indicates that dosages and amounts outside those specified may also be effective and safe, and such dosages and amounts are also encompassed by the scope of the present claims.

A therapeutic agent (or the therapeutic agents) of the present invention is used in a method, kit, combination, and/or composition in a "disorder-effective amount." A "disorder-effective amount" is intended to qualify the amount of an agent (or agents) required to treat or prevent a disorder in a subject, or relieve to some extent one or more of the symptoms associated with, or related to, a disorder in a subject. In a mammal, this includes, but is not limited to, improving or alleviating the above stated diseases.

The term "prevent" or "prevention," in relation to a disorder, means no disorder, condition, or disease development if none had occurred, or no further disorder, condition, or disease development if there had already been development of a disorder, condition, or disease.

The term "disorder-effective amount" means that the dose of a therapeutic agent (or agents) is such that a therapeutic level of agent is delivered to the bloodstream over the term that the composition is to be used. Such delivery is dependent on a number of variables including the time period for which the individual dosage unit is to be used, or the flux rate of the therapeutic agent into the systemic circulation of the subject. It is to be understood that specific dose levels of a therapeutic agent for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially provide useful guidance on the proper doses for subject administration. Studies in animal models are often used for guidance regarding effective dosages for treatment of a disorder in accordance with a particular agent. In terms of treatment protocols, it should be appreciated that the dosage to be administered will depend on several factors, including the particular agent that is administered, the route administered, the physical state of the particular agent, the condition of the particular subject, etc.

Example

By measuring the potency of the *cannabis* hash concentrate, it is possible to consistently blend the capsules into specific strengths as measured by milligrams of THC in that capsule. For example, if the potency of the *cannabis* component is 42% (wt), this means there are 420 milligrams of THC per gram of the *cannabis* component. To produce a capsule containing 30 milligrams of THC, my composition must be blended to contain $1/14^{th}$ of a gram of *cannabis* component (420/30=14). The composition for a 60 milligram strength THC capsule is blended to contain $1/7^{th}$ of a gram (420/60=7) of the *cannabis* component. The composition for a 100 milligram strength THC capsule will contain 1/4.2th of a gram (420/100=4.2) capsules per gram of the *cannabis* component.

Batches of the composition may conveniently be blended in quantities adequate to produce 1,000 capsules. This batch size helps to ensure uniform homogeneity in the mixture and allows for accurate production tracking. Production tracking notes the date of manufacture, the *cannabis* strain, and a code referring back to the laboratory testing report for potency, absence of pesticides, and CFU count.

To produce 1,000 capsules containing 30 milligram strength THC, the calculations are as follows: 30 mg. THC×1,000 capsules=30,000 mg. of THC. If the *cannabis* component in this example tested at 42% potency, it contains 420 mg. of THC per gram of *cannabis* component, an amount (30,000/420) equaling 71.43 grams of *cannabis* component is required to make 1,000 capsules. For 30 mg. and 60 mg. strengths I use either gelatin or vegetarian size 0 (zero) capsules. For 100 mg. strength I use gelatin or vegetarian size 00 (zero zero) capsules. A size 0 capsule is calculated to hold 0.44 grams of blended medicine. A size 00 capsule is calculated to hold 0.62 grams of blended medicine.

My formulation typically uses 0.10 grams of soy lecithin in each capsule for all three strengths—30, 60, and 100 mgs. Soy lecithin at 0.10 grams per capsule is a constant in this example of the composition. The amount of *cannabis* component used depends on a combination of the potency measured in the laboratory (for example 42%) and the production strength—30, 60, or 100 mg. The third component (hemp seed powder) is added by weight so that the total blended formulation of each of the 30 and 60 mg. strengths weighs exactly 440 grams for a production run of 1,000 capsules. The total blended formulation for the 100 mg strength will be exactly 620 grams.

Therefore, for a *cannabis* component potency of 42% (wt) and a production of 1,000 capsules at 60 mg strength, the weights of each component would be as follows:

a.) 60 mg. of THC per capsule×1,000 capsules=60,000 mgs. of THC.
b.) 60,000/420 (42% potency)=143 grams of *cannabis* component
c.) plus 100 grams of soy lecithin=243 grams.
d.) the total weight needed to fill a size 0 capsule is 440 grams; the amount of hemp seed powder needed is calculated by: 440−143−100=197 grams of hemp seed powder.

Utilizing a higher potency *cannabis* component means that a smaller amount of *cannabis* component is needed in the formulation. For example using a *cannabis* component of 60% (600 mg per gram of *cannabis* component) only 100 grams of *cannabis* component is needed. The 1,000 capsules will still contain 100 grams of soy lecithin. But the amount of hemp seed powder needed to fill the 1,000 capsules is increased to 240 grams.

What is claimed is:

1. A powdered composition comprising:
   powdered hemp seed,
   lecithin, and
   a THC concentrate consisting essentially of *cannabis* trichomes, and
   wherein at least the lecithin and the THC concentrate have been heated together under conditions suitable for converting at least a portion of any THC-carboxylate in the THC concentrate to THC and to produce the powdered composition at the completion of the heating step, and
   wherein the THC concentrate contributes substantially all of the THC to the powdered composition.

2. The powdered composition of claim 1 where the lecithin comprises soy or sunflower lecithin.

3. The powdered composition of claim 1 where the composition is in the form of a hard-shelled gelatin or plant vegetarian capsule or tablet.

4. The powdered composition of claim 1 further comprising one or more excipients.

5. A kit comprising the powdered composition of claim 1 in multiple dosage forms, a package, and directions for use.

6. The powdered composition of claim 1 wherein the powdered hemp seed, lecithin, and THC concentrate have been heated together under conditions suitable for converting at least a portion of any THC-carboxylate in the THC concentrate to THC.

7. The powdered composition of claim 1 where the composition is further formed into the physical form of a tablet.

8. The powdered composition of claim 1 where the composition further comprises a gelatin or plant vegetarian capsule encompassing the powdered hemp seed, lecithin, and THC concentrate.

9. A kit comprising multiple substantially equal doses of the powdered composition of claim 1 and wherein each dose of the composition contains a substantially equal amount of THC.

10. A kit of claim 9 further comprising packaging and directions for use.

11. A powdered composition consisting essentially of:
    powdered hemp seed,
    lecithin, and
    a THC concentrate consisting essentially of *cannabis* trichomes, and
    wherein at least the lecithin and the TI-IC concentrate have been heated together under conditions suitable for converting at least a portion of any THC-carboxylate in the THC concentrate to THC and to produce the powdered composition at the completion of the heating step.

12. The powdered composition of claim 11 where the lecithin comprises a soy, or sunflower lecithin.

13. The powdered composition of claim 12 wherein the powdered hemp seed, lecithin, and THC concentrate have been heated together under conditions suitable for converting at least a portion of any THC-carboxylate in the THC concentrate to THC.

14. The powdered composition of claim 11 further comprising one or more excipients.

15. The powdered composition of claim 11 where the composition is in the physical form of a tablet.

16. The powdered composition of claim 11 where the composition further comprises a gelatin or plant vegetarian capsule encompassing the powdered hemp seed, lecithin, and THC concentrate.

17. A kit comprising multiple substantially equal doses of the powdered composition of claim 11 and wherein each dose of the composition contains a substantially equal amount of THC.

18. The kit of claim 17 further comprising packaging and directions for use.

19. A powdered product made by the process of:
    (a) mixing hemp seed, lecithin, and a THC concentrate consisting essentially of *cannabis* trichomes containing THC-carboxylate to form a mixture,
    (b) grinding the mixture formed in step (a), and
    (c) heating the ground mixture to decarboxylate at least a portion of the THC-carboxy present in the THC concentrate and to produce the powdered composition at the completion of the heating step.

20. The powdered product of claim 19 wherein the process further comprises the step of introducing the product of step (c) into hard-shelled gelatin or plant vegetarian capsules or forming said product into tablets.

21. The powdered product of claim 19 where the lecithin comprises soy or sunflower lecithin.

22. A powdered product made by the step of heating a powdered and ground mixture of hemp seed, lecithin, and a THC concentrate consisting essentially of *cannabis* trichomes containing THC-carboxylate to de-carboxylate at least a portion of the THC-carboxyl present in the THC concentrate and to produce the powdered composition at the completion of the heating step.

23. The powdered product of claim 22 further comprising hard-shelled gelatin or plant vegetarian capsules encompassing the powdered product or wherein said product is formed into tablets.

24. The powdered product of claim 22 where the lecithin comprises soy or sunflower lecithin.

25. The powdered composition of claim 1 wherein the THC concentrate is formed by the process of immersing and chilling *cannabis*-containing plant material in ice water to harden resinous THC-containing trichomes, agitating the chilled *cannabis*-containing plant material to detach the resinous THC-containing trichomes, and separating the resinous THC-containing trichomes from the remaining plant material to form the THC concentrate.

26. The powdered composition of claim 11 wherein the THC concentrate is formed by the process of immersing and chilling *cannabis*-containing plant material in ice water to harden resinous THC-containing trichomes, agitating the chilled *cannabis*-containing plant material to detach the resinous THC-containing trichomes, and separating the resinous THC-containing trichomes from the remaining plant material to form the THC concentrate.

27. The powdered composition of claim 19 wherein the THC concentrate is formed by the process of immersing and chilling *cannabis*-containing plant material in ice water to harden resinous THC-containing trichomes, agitating the chilled *cannabis*-containing plant material to detach the resinous THC-containing trichomes, and separating the resinous THC-containing trichomes from the remaining plant material to form the THC concentrate.

* * * * *